US005759787A

United States Patent [19]

Strulovici

[11] Patent Number: 5,759,787
[45] Date of Patent: Jun. 2, 1998

[54] KINASE ASSAY

[75] Inventor: Berta Strulovici, Sunnyvale, Calif.

[73] Assignee: Tularik Inc., South San Francisco, Calif.

[21] Appl. No.: 702,970

[22] Filed: Aug. 26, 1996

[51] Int. Cl.$^6$ .................... G01N 33/573; G01N 33/53; G01N 33/543
[52] U.S. Cl. .................... 435/7.4; 435/7.5; 435/4; 435/968; 436/517
[58] Field of Search .................... 435/4, 7.1, 7.2, 435/7.21, 7.4, 7.5, 7.7, 7.72, 7.92, 7.94, 287.2, 15, 968, 518, 802; 436/517

[56] References Cited

U.S. PATENT DOCUMENTS

| | | | |
|---|---|---|---|
| 5,223,402 | 6/1993 | Abbas | 435/18 |
| 5,441,894 | 8/1995 | Colemena et al. | 436/518 |
| 5,610,016 | 3/1997 | Sato et al. | 435/6 |
| 5,641,635 | 6/1997 | Emmons et al. | 435/6 |
| 5,657,118 | 8/1997 | Lee | 356/246 |

OTHER PUBLICATIONS

Yano, T. et al. A Monoclonal Antibody to the Phosphorylated Form of Glial Fibrillary Acidic Protein: Application to a Non–Radioactive Method for Measuring Protein Kinase Activities. Biochem. Res. Com. 29 Mar. 1991, vol. 175, No. 3, p. 1144–1151.

*Primary Examiner*—Susan A. Loring
*Attorney, Agent, or Firm*—Richard Aron Osman

[57] ABSTRACT

The invention provides novel methods and compositions for detecting kinase activity in solution, without the use of radioactivity. The methods marry the kinetic advantages of solution-based reaction with the efficiency and high-throughput adaptability of solid-phase wash and detection steps, yet is conveniently practiced in a single tube. The methods may be used to assay for kinase activity per se or, by controlling for the kinase activity, for modulators of kinase activity. The method is exemplified with a preferred chemiluminescent protein kinase assay using biotinylated substrate peptides captured on a streptavidin coated microtiter plate and monoclonal antibodies to detect their phosphorylation.

11 Claims, 6 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

Leu Arg Arg Ala Ser Leu Gly
    1                5

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

Arg Arg Arg Val Thr Ser Ala Ala Arg Arg Ser
    1                5                          10

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

Phe Arg Arg Leu Ser Ile Ser Thr
    1                5

( 2 ) INFORMATION FOR SEQ ID NO:4:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

-continued

| Met | Asp | Arg | Gln | Thr | Lys | Gln | Gln | Pro | Arg | Gln | Asn | Val | Ala | Tyr | Asn |
| 1 | | | | 5 | | | | | 10 | | | | | 15 | |
| Arg | Glu | Glu | Glu | Arg | Arg | Arg | Arg | Val | Ser | His | Asp | Pro | Phe | Ala | Gln |
| | | | 20 | | | | | 25 | | | | | 30 | | |
| Gln | Arg | Pro | Tyr | Glu | Asn | Phe | | | | | | | | | |
| | | 35 | | | | | | | | | | | | | |

1

KINASE ASSAY

INTRODUCTION

1. Field of the Invention

The invention relates to methods for detecting kinase (an enzyme) activity.

2. Background

Protein kinases represent one of the largest group of enzymes, with critical role in many cellular signal transduction processes. Due to genome projects and other recent developments in molecular biology techniques, new kinases with uncharacterized biochemical properties and substrate specificity are discovered more and more frequently. Thus, a sensitive assay measuring the activity of these enzymes would be of great value. Traditional protein kinase assays include the use of labeled ATP as phosphate donor, and a substrate peptide as phosphoacceptor containing the respective kinase recognition motif. Following the kinase reaction the substrate peptide is captured on an appropriate filter paper. Unreacted labeled ATP and metabolites are resolved from the radioactive peptide substrate by various techniques, involving trichloroacetic acid precipitation and extensive washing. Addition of several positively charged residues allows capture on phosphocellulose paper followed by washing. Radioactivity incorporated into the substrate peptide is detected by scintillation counting (1). This assay is relatively simple, reasonably sensitive, and the peptide substrate can be adjusted both in terms of sequence and concentration to meet the assay requirements. But it also has several drawbacks: it generates radioactive waste; radioactive ATP has a half-life of only 14 days; the assay is sensitive only at low micromolar concentrations of cold ATP, while the intracellular ATP concentration is in the millimolar range; and, to achieve an appropriate signal the peptide substrate has to be used at around its $K_m$ value, which is about 5–20 µM even for the best substrates of well characterized kinases (2), while the intracellular concentration of the endogenous polypeptide substrates is presumably much lower. The subphysiological ATP and supraphysiological substrate concentrations of this assay may have adverse effect on attempts to develop inhibitors efficient under the much different in vivo conditions.

Several approaches have been tried to overcome these limitations. Some of them used synthetic peptide substrates and non-radioactive detection of their phosphorylation by fluorescence, spectrophotometry, or other methods (3–8). However, these methods are either insensitive, or quite laborious and not amenable to automation. Alternative phosphopeptide capture methods have also been tried, but these assays are still based on radioactive detection (9, 10). Cell based assays have also been developed as a read-out for the activities of various protein kinases. These approaches work under physiological conditions, but are generally much more complicated, prone to various sources of error, and the real target of a drug lead compound may not even be related to the kinase of interest (11–13). The availability of phosphotyrosine antibodies allowed the development of colorimetric ELISA assays for detection of protein tyrosine kinases using polypeptides as substrates (14–18). In addition to being non-radioactive, this approach generally proved to be sensitive and easy to automate, providing a good alternative for tyrosine kinases.

SUMMARY OF THE INVENTION

The invention provides novel methods for detecting kinase activity in solution, without the use of radioactivity. The subject methods marry the kinetic advantages and sensitivity of solution-based reaction with the efficiency, cost-effectiveness and high-throughput adaptability of solid-phase wash and detection steps, yet is conveniently practiced in a single tube. The methods may be used to assay for kinase activity per se or, by controlling for the kinase activity, for modulators of kinase activity. In addition, the invention provides kits for kinase modulator screening which include premeasured amounts of the compositions used in the disclosed methods. The general methods involve steps:

a) incubating a solution comprising a kinase, a substrate of the kinase wherein the substrate comprises a phosphorylation-independent first tag, a first receptor, and a nucleoside triphosphate, under conditions whereunder the kinase phosphorylates the substrate in solution to form a product comprising the first tag, (and usually most of the substrate), and a phosphorylation-dependent second tag;

b) further incubating the solution under conditions whereunder the first receptor immobilizes the product on a solid substrate by specifically binding one of the two tags to form a first immobilized conjugate comprising the first receptor and the product;

c) washing the solid substrate;

d) contacting the first immobilized conjugate with a second receptor under conditions whereunder the second receptor specifically binds the other one of the two tags to form a second immobilized conjugate comprising the first receptor, the product and the second receptor;

e) washing the solid substrate;

f) detecting the second receptor;

wherein the presence of the second receptor indicates the presence of the product and the presence of the product indicates the presence of the kinase activity.

For modulator screens, the solution further comprises a candidate agent and the initial incubation is under conditions whereby, but for the presence of the candidate agent, the kinase (or kinases) phosphorylates the substrate at a first, control kinase activity and so converts at least a detectable portion, and preferably, substantially all of the initial amount of substrate into product, whereby a final amount of the substrate remains. As such, depending on the stop point of the reaction, the measured activity may reflect a catalytic rate or an equilibrium constant. For these assays, a difference between the kinase activity in the presence and absence of the agent indicates that said candidate agent modulates the activity of the targeted kinase.

A wide variety of kinases, substrates, tags, receptors, labels may be used. Preferred kinases for use in the methods are protein kinases and preferred substrates are peptide or protein substrates. According to one preferred embodiment, the first tag is biotin, one of the receptors is avidin or an avidin-like protein such as streptavidin, the second tag is a phosphorylated serine or tyrosine and the other receptor is an antibody which specifically binds the product at the phosphorylated amino acid. A wide variety of means may be used for detecting the second receptor. Preferred means are cost-effective and readily automated for high-throughput analysis, such as optical detection. For example, the second receptor may comprise a label, such as an enzyme which enzyme catalyzes a chromogenic or chemiluminogenic reaction. Alternatively, the second receptor can be detected by the use of a third labeled receptor which specifically binds the second receptor.

The method is exemplified with a preferred chemiluminescent protein kinase assay using biotinylated substrate peptides captured on a streptavidin coated microtiter plate and monoclonal antibodies to detect their phosphorylation. Assay conditions were optimized and validated for sensitive measurement of protein kinase A (PKA), protein kinase C (PKC), $Ca^{2+}$/calmodulin-dependent protein kinase II (CAMKII), and src activities. The chemiluminescent detection has several advantages over currently used radioactive or colorimetric methods. The assay is fast, very simple to perform, and easily adaptable to automation and high-throughput drug screening. It provides high sensitivity and robust signal using low concentrations of enzyme and substrate. Signal amplitude shows positive correlation with ATP concentration, thus allowing the assay to function at high, close to physiological ATP levels, in contrast to the radioactive method. Overall, among the presently available methods for the detection of protein kinase activity, chemiluminescence was found to provide the highest sensitivity under conditions most closely mimicking the intracellular environment.

DETAILED DESCRIPTION OF THE INVENTION

Figure 1A:
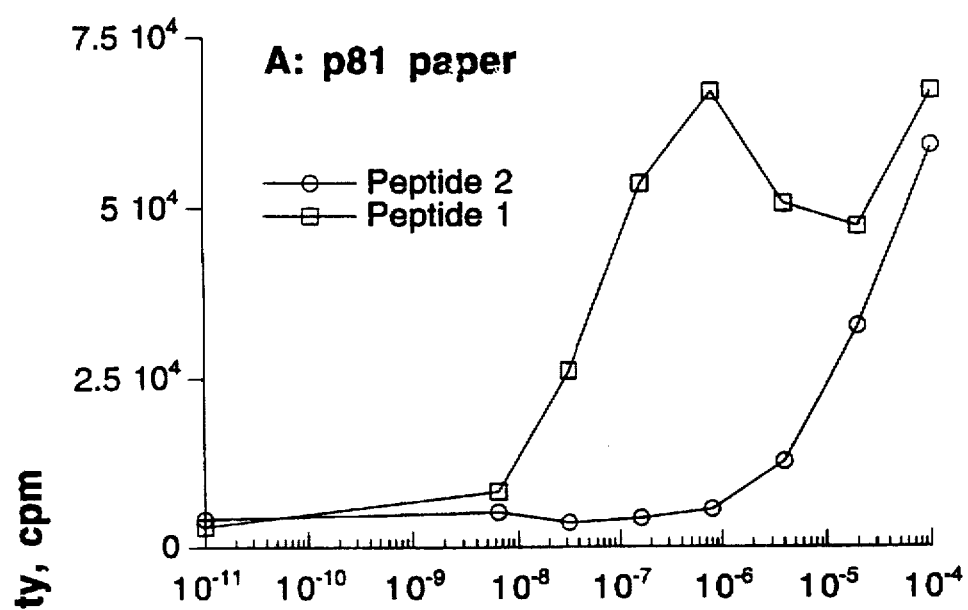
FIGS. 1A and 1B. Comparison of capturing substrate peptides by p81 phosphocellulose paper (FIG. 1A) and streptavidin coated microtiter plate (FIG. 1B).

The invention provides efficient and sensitive methods and compositions for detecting, identifying and/or characterizing kinase activity and specific modulators of kinase activity, preferably protein kinase activity. The methods use a bifunctional kinase reaction product to 1) specifically capture and immobilize phosphorylated product as opposed to unreacted substrate and to 2) specifically detect the immobilized product as opposed to other immobilized molecules. One functionality of the product is provided by the phosphorylation reaction itself: the reaction introduces a novel molecular structural feature, or epitope, within the substrate, for which feature a specifically binding receptor is available. Conveniently, this feature comprises the phosphate group itself; for example, a phosphorylated serine or tyrosine residue of a peptide substrate. Alternatively, phosphorylation (or dephosphorylation, as the reaction can generally be run in reverse) of the substrate may induce a specifically-detectable conformational change which does not necessarily comprise the phosphate group. The assay may use any phosphorylation-dependent feature for which a specifically binding receptor can be obtained. Specific immune receptor, such as an antibody provide convenient such receptors.

The other functionality is effected by using a substrate comprising a phosphorylation-independent molecular tag, different from the phosphorylation-dependent feature, for which a specifically-binding receptor is available. Exemplary substrate tags include peptide epitope tags such as FLAG, myc or His, for which specific antibodies are conveniently available, carbohydrate tags for which specific lectins are conveniently available, or other convenient, high-affinity ligand/receptor pairs, such as biotin/avidin. In any event, the generation of the phosphorylation-dependent feature does not preclude the specificity of the binding between the phosphorylation-independent tag and its corresponding receptor. Similarly, the binding of the first receptor to the product does not preclude the specificity of the binding of the second receptor to the product. In addition, the tags are sufficiently different to avoid cross-reactivity with the receptors.

In addition to the kinase, substrate, NTP, and first receptor, the reaction mixture may also comprise a candidate agent such as a preselected kinase inhibitor or, especially for high-throughput drug screening, a library-derived candidate agent. Library-derived candidate agents encompass numerous chemical classes, though typically they are organic compounds; preferably small organic compounds. The libraries may comprise synthetic and/or naturally derived compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs. The agent is provided in standard serial dilutions or in an amount determined by analogy to known modulators. In addition, the mixture usually includes additional reagents, such as salts, buffers, etc. to facilitate or maximize kinase activity.

A wide variety of solid substrates may be used. Factors to be considered in selecting an appropriate substrate include the adhesion and functional retention of the immobilizing receptor, accessible surface area for binding, wash convenience, cost, high-throughput adaptability, etc. Frequently, the solid substrate will be the wall of the reaction reservoir itself. Preferred substrates maximize signal strength and the signal-to-noise ratio. Exemplary substrates include polystyrene microtiter plates, fine fibers, polymeric or silica-based microbeads, etc., preferably pre-activated to provide maximal protein binding. When used, microbeads are selected by size, range and structure to maximize surface area, filter retention and bead suspension time during the assay incubations.

A wide variety of reaction conditions can be employed depending on the targeted kinase(s); in vitro conditions to support activity of exemplary kinases are exemplified below and/or otherwise known in the art. For example, the reaction generally requires the presence of an effective amount of a nucleoside triphosphate, such as ATP. For many mammalian kinases, the reaction is carried out at room or elevated temperatures, usually in the range of 20° to 40° C., conveniently at room (ca. 25° C.) temperature. For high-throughput applications, reactions time is minimized, and is usually from 0.1 to 4 hours, more usually about 0.5 to 1.5 hours. Importantly, the kinase reaction occurs in solution. Hence, for single-tub assays where the conditions to effect phosphorylation are the same as those which effect immobilization, the rate of phosphorylation preferably exceeds the rate of immobilization sufficient to ensure a solution-phase kinase reaction.

The wash steps of the methods involve separating unbound components from the immobilized product conjugates, usually by rinsing one to five times with a buffered medium. The method used for separating and washing depends on the nature of the reaction reservoir and solid substrate. For example, where the substrate is in the form of aggregated fibers, the solid phase may be physically transferred from the reaction reservoir to a series of rinse reservoirs. With beads, the separating and washing steps are conveniently performed by filtration, frequently vacuum-assist or centrifugation.

A variety of methods may be used to detect the label depending on the nature of the label and other assay components. Labels may be directly detected through optical or electron density, nonradiative energy transfers, etc., or indirectly through the a binding or reaction with a reagent which, in turn, provides a detectable signal. For example, the second receptor may be decorated with one or more (for signal amplification) reagents such as secondary antibodies conjugated to an enzyme for an ELISA-type assay.

The disclosed methods are particularly suited to automated high throughput drug screening. In a preferred embodiment, the individual sample incubation volumes are less than about 500 µl, preferably less than about 250 µl, more preferably less than about 100 µl. Such small sample volumes minimize the use of often scarce candidate agent, expensive enzymes, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the assays' steps. The computer is loaded with software which provides the instructions which direct the arm and work station operations and provides input (e.g. keyboard and/or mouse) and display (e.g. monitor) means for operator interfacing.

The following experimental section is offered by way of illustration and not by way of limitation.

EXAMPLES

Example 1: Materials

The following reagents were used: PKA catalytic subunit (Sigma); protein kinase C (PKC, a mixture of α, β, and γ isoforms), src, and the monoclonal antibodies 4G10 and MPM-2 (Upstate Biotechnology); $Ca^{2+}$/calmodulin-dependent protein kinase II (CAMKII, New England Biolabs); colorimetric kit for the detection of PKA and PKC activity, containing the YC10 monoclonal antibody anti-phospho GFAP, recognizing phosphoserine in the context of TS(P)AARR (Panvera). The same antibody was also purchased separately. Alkaline phosphatase conjugated goat anti-mouse antibody (Tropix or Pierce); chemiluminescent substrate CSPD+Sapphire II (Tropix); [$\gamma$-$^{32}$P]ATP (Du Pont NEN); streptavidin coated black microtiter plates (Labsystems or Xenopore); P81 phosphocellulose paper (Whatman). All kinase inhibitors were from LC Laboratories.

Example 2: Peptide synthesis

Peptides were synthesized on an automated synthesizer using solid-phase FMOC chemistry with HBTU/HOBT activation (19). Amino caproic acid was used as a spacer between the biotin and the N-terminus of the peptide. Peptides were cleaved from the solid support and deprotected using reagent K (20) and then were purified using reverse phase HPLC. Electrospray mass spectrometry and analytical RP-HPLC were used for QC of the peptides. The following peptides were used as protein kinase substrates:

peptide 1: bio-LRRASLG (SEQ ID NO:1) (Kemptide)

peptide 2: bio-RRRVTSAARRS (SEQ ID NO:2) (PKA and PKC substrate peptide derived from glial fibrillary acidic protein)

peptide 3: bio-FRRLSIST (SEQ ID NO:3) (CAMK II substrate peptide derived from phosphorylase kinase)

peptide 4: bio-MDRQTKQQPRQNVAYNREEERRRRVSHD-PFAQQRPYENF (SEQ ID NO:4) [derived from RIP (21)]

Example 3: PKA kinase reaction

The peptide substrates were added in 90 µl assay buffer containing 20 mM Tris-HCl pH 7.5, 2.5 mM $MgCl_2$, and 100 µM ATP for non-radioactive detection, or 10 µM cold ATP supplemented with 0.5 µCi/well [$\gamma$-$^{32}$P]ATP for radioactive detection, unless indicated otherwise. Freshly reconstituted PKA (1.25 ng/well in 10 µl, unless indicated otherwise) was added last and the samples were incubated for 30 minutes at room temperature. Depending on the detection method the samples were further processed as described below.

Example 4: PKC kinase reaction

Peptide 2 was added in 90 µl assay buffer containing 20 mM Tris-HCl pH 7.5, 2.5 mM $MgCl_2$, 50 µM $CaCl_2$, 10 µg/ml phosphatidylserine, 20 µM ATP, with or without inhibitors. PKC (0.25 ng/well in 10 µl) was added last, and the kinase reaction was allowed to proceed for 30 minutes at room temperature. Then chemiluminescent detection using YC10 antibody was performed as described below.

Example 5: CAMKII kinase reaction

Peptide 3 ($10^{-6}$M) was added in 90 µl assay buffer containing 20 mM Tris-HCl pH 7.5, 10 mM $MgCl_2$, 2 mM $CaCl_2$, 1 mM DTT, 0.1 mM EDTA, 100 µM ATP, 100 U calmodulin. CAMKII was added last in 10 µl, and the samples were incubated for 30 minutes at room temperature. Chemiluminescent detection using MPM-2 antibody was performed as described below.

Example 6: SRC kinase reaction

Peptide 4 was added in 90 µl assay buffer containing 100 mM Tris-HCl pH 7.5, 25 mM $MnCl_2$, 2 mM EGTA, 0.25 mM $Na_3VO_4$, 125 mM Mg acetate, and 100 µM ATP for non-radioactive detection, or 10 µM cold ATP supplemented with 0.5 µCi/well [$\gamma$-$^{32}$P]ATP for radioactive detection. src was added last (3 unit/well in 10 µl), kinase reaction was performed at room temperature for 30 minutes, and depending on the detection method, the samples were further processed as described below.

Example 7: Radioactive detection

After performing a PKA kinase reaction for 30 minutes, the samples were divided into two. 50 µl were transferred into wells of streptavidin coated microtiter plates, to allow the capture of the biotinylated peptides for additional 50 minutes. The wells were washed five times with water, dried, broken into scintillation vials and counted. The other half of the reaction mixture was further incubated in the original plate for 50 minutes, then TCA was added to the reaction mixture (10% final concentration) and 30 µl was spotted onto P81 paper (1×1 inch squares). After 20 minutes the squares were washed three times with water, dried, placed into scintillation vials and counted. A microtiter plate version of the phosphocellulose capture method was also used with similar results. For src only the phosphocellulose capture method was used.

Example 8: Colorimetric and chemiluminescent detection

The substrate peptides were initially captured onto streptavidin coated plates prior to the kinase reaction. In later experiments the two reactions were performed simultaneously. Upon completion of the kinase reaction the wells were washed five times with PBS containing 0.2% Tween-20 (T-PBS). Primary antibody (YC10 at 1:10,000 dilution for peptide 2, MPM-2 at 1:2,000 dilution for peptide 3, and 4G10 at 1:2,000 dilution for peptide 4) was added in T-PBS for 30 minutes, then the plate was washed 5 times with T-PBS. Secondary anti-mouse antibody (horseradish peroxidase conjugated for calorimetric, or alkaline phosphatase conjugated for chemiluminescent detection) was added at 5000-fold dilution in T-PBS supplemented with 0.2% BSA for 30 minutes, after which the plate was washed five times in T-PBS. In later experiments the primary and secondary antibodies were premixed and added together for 40 minutes. Colorimetric reaction was performed for 5 minutes with o-phenylenediamine substrate, stopped, and the plate was read in a Bio Kinetics Reader EL 340 microplate reader (Bio Tek Instruments) at 492 nm. For chemiluminescent detection CSPD+Sapphire II was added at a threefold dilution in diethanolamine buffer (pH: 10), and after 10 minutes the plate was read with a Luminoskan EL microtiter plate luminometer (Labsystems) or Packard scintillation counter.

Example 9: Results

Figure 1B:
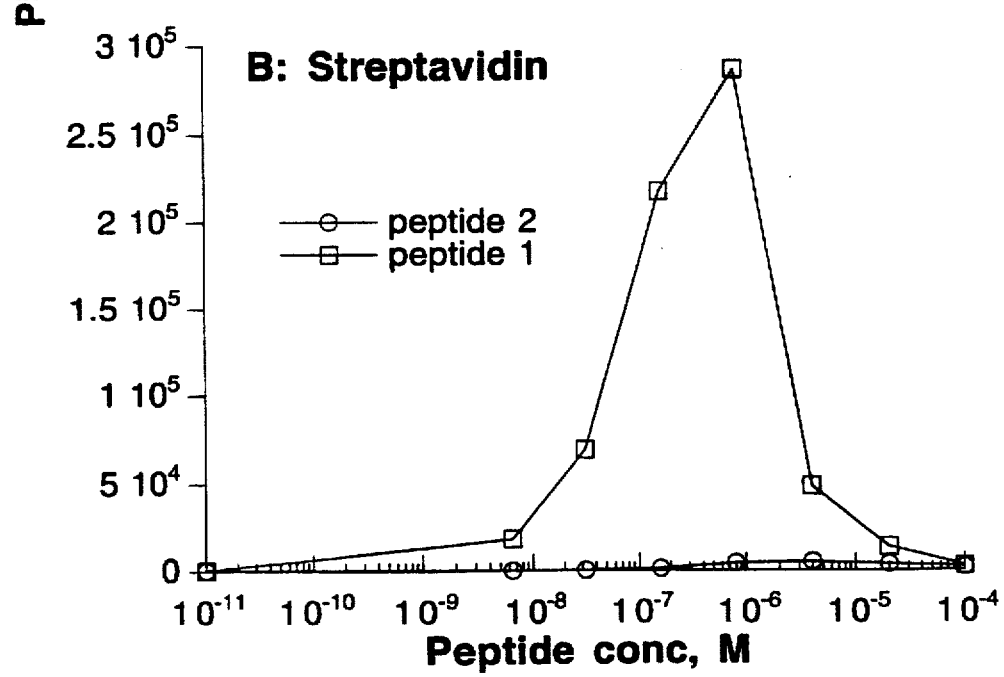

While filtration assays generally require one plate for reaction, and another for filtration, ELISA-type assays can be performed in a single plate, and thus are easier to automate. For this reason we wanted to establish an ELISA-type protein kinase assay, where the capture of the phosphorylated product is based on the strong binding and high selectivity of streptavidin to biotin. The binding and phosphorylation characteristics of two biotinylated PKA substrate peptides, kemptide (peptide 1) and a peptide derived from glial fibrillary acidic protein (peptide 2), were compared (FIG. 1). Following the radioactive PKA reaction the two peptides were captured either by the traditional phosphocellulose paper method or by streptavidin immobilized on a microtiter plate. Much higher PKA activity was detected using peptide 1 as substrate with both capture methods, in agreement with published data describing kemptide as the best substrate for this kinase (2). Because of its unfavorable kinetic properties the $K_m$ of peptide 2 can not be determined by this experiment, but it is definitely above 20 µM. At $10^{-6}$M peptide concentration the binding efficiency of peptide 1 to streptavidin was much higher than to phosphocellulose, which require large number of positive charges. Hence, the more positively charged peptide 2 showed better binding to phosphocellulose. With both peptides, streptavidin capturing resulted in a decline in scintillation counts above $10^{-6}$ M peptide concentration. This is attributable to competition of phosphorylated and nonphosphorylated biotinylated peptides to a limited number of streptavidin binding sites, and was found to occur when the number of biotin molecules exceeds the number of streptavidin binding sites (the latter information provided by the manufacturer of the streptavidin coated plate). Overall, use of peptide 1 combined with streptavidin capture resulted in good sensitivity, while the results generated with peptide 2 were much weaker.

Figure 2:
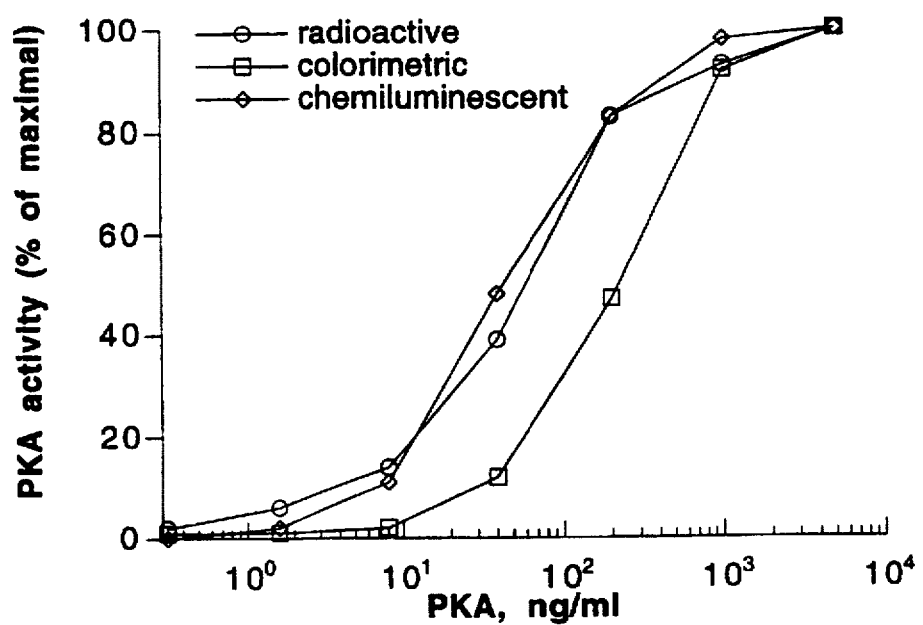
FIG. 2. Comparison of three methods for the detection of PKA enzymatic activity.

A monoclonal antibody (YC10) recognizing phosphoserine in the context of TS(P)AARR has recently become commercially available. Since peptide 2 contains this sequence motif, we attempted to detect PKA activity by using this antibody. The kinase reaction was performed in microtiter plates containing the preimmobilized peptide. Then the plate was incubated with the YC10 antibody, peroxidase or alkaline phosphatase conjugated secondary antibody was added, and either a colorimetric or a chemiluminescent detection reaction was performed. To compare the sensitivity of radiolabel, colorimetry and chemiluminescence as detection systems, a dose response of PKA was performed with peptide 2 (FIG. 2) or peptide 1. The chemiluminescent assay was more sensitive than colorimetry, and more sensitive, or at least as sensitive as the radioactive assay using peptide 2, or peptide 1, respectively.

Figure 3:
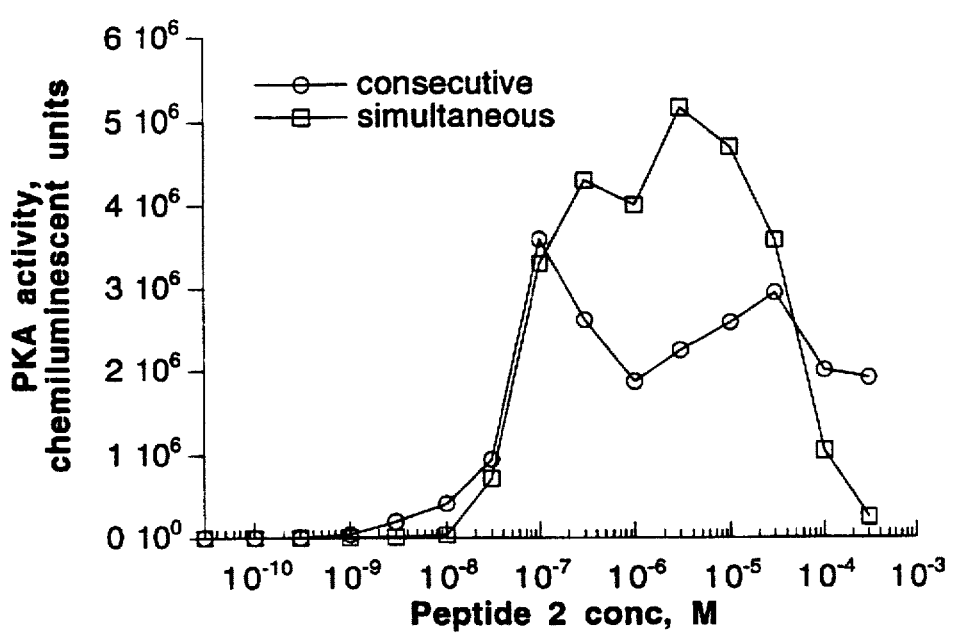
FIG. 3. Comparison of solid phase versus homogenous kinase assays.

Next we attempted to reduce the number of steps in the more sensitive chemiluminescent assay. We found that preincubation of the streptavidin plate with the biotinylated peptide substrate was not necessary: even higher sensitivity was achieved when the peptide binding and phosphorylation reactions were performed simultaneously, while the peptide and kinase were in solution (FIG. 3). With both approaches strong signal was observed at peptide concentration as low as $10^{-7}$M. Again, above $10^{-6}$M peptide concentration a decline in assay sensitivity was detected, presumably due to limiting biotin binding sites. Furthermore, consecutive incubations with the two antibodies can also be replaced by adding the two antibodies together, without any loss in sensitivity.

Figure 4:
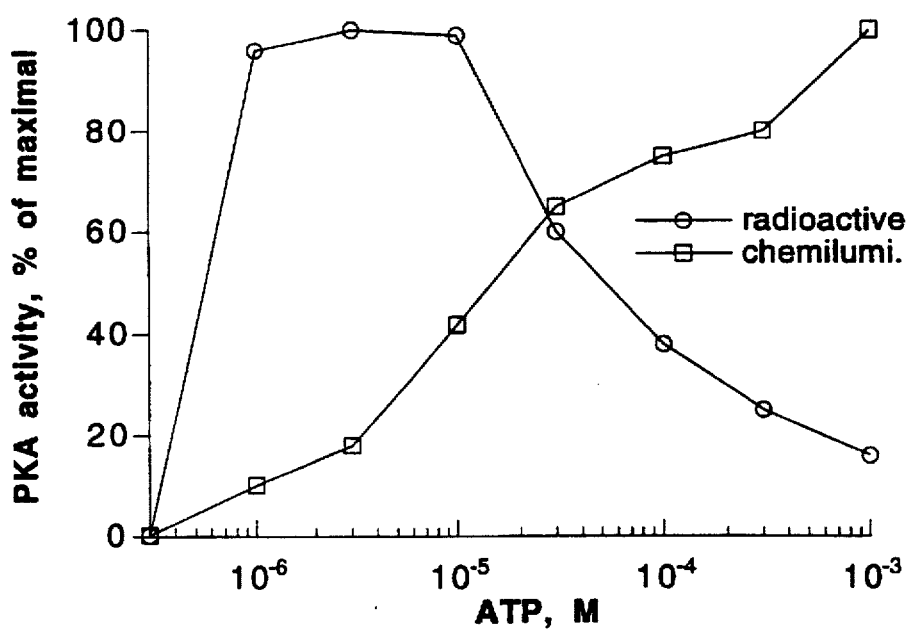
FIG. 4. ATP dependence of the radioactive and chemiluminescent PKA assays.

One of the major drawbacks of the radioactive assay is its inefficiency at close to physiological ATP concentrations, due to the diluting effect of high concentration of cold ATP on the radiolabelled one. The ATP dependence of the chemiluminescent assay was also tested. It was found to be sensitive at low micromolar ATP concentrations, but in contrast to the radioactive assay, the activity increased in an ATP-dependent manner (FIG. 4).

Figure 5A:
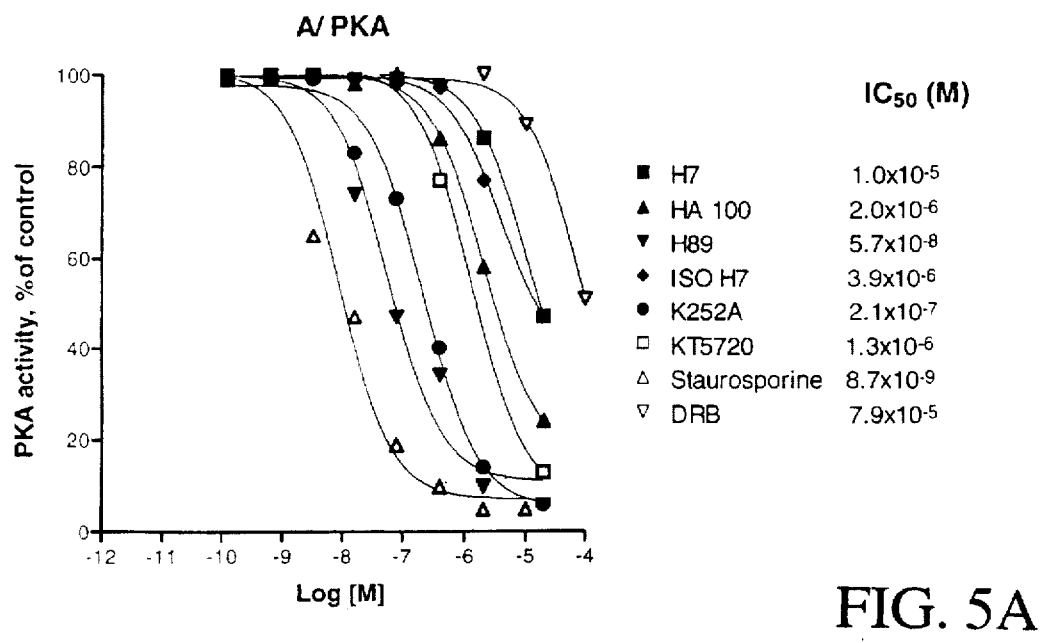
FIGS. 5A and 5B. Effect of known inhibitors on PKA and PKC activity using chemiluminescent detection.
Figure 5B:
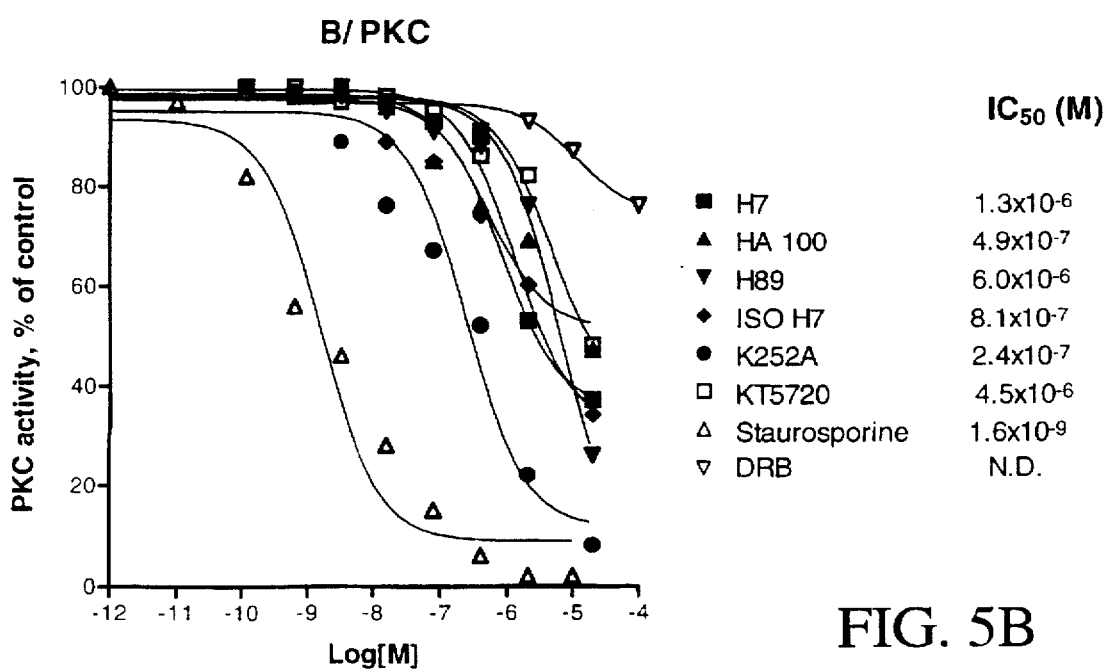

The chemiluminescent assay was validated using a panel of known kinase inhibitors. Since PKC activity was also found to be easily detectable by this assay (data not shown), it was also included in this experiment. As shown in FIG. 5, when the kinase reactions were performed in the presence of 20 µM ATP, $IC_{50}$ values similar to published data were obtained. At 100 µM ATP, while the assay itself was more sensitive, substantial loss of potency was observed for most of the tested inhibitors (data not shown). This result is expected, since most of these inhibitors are known to compete with ATP by binding to the ATP binding site of the kinase. As intracellular ATP concentrations are much higher (mM range) these inhibitors show much weaker potency in vivo.

Figure 6A:
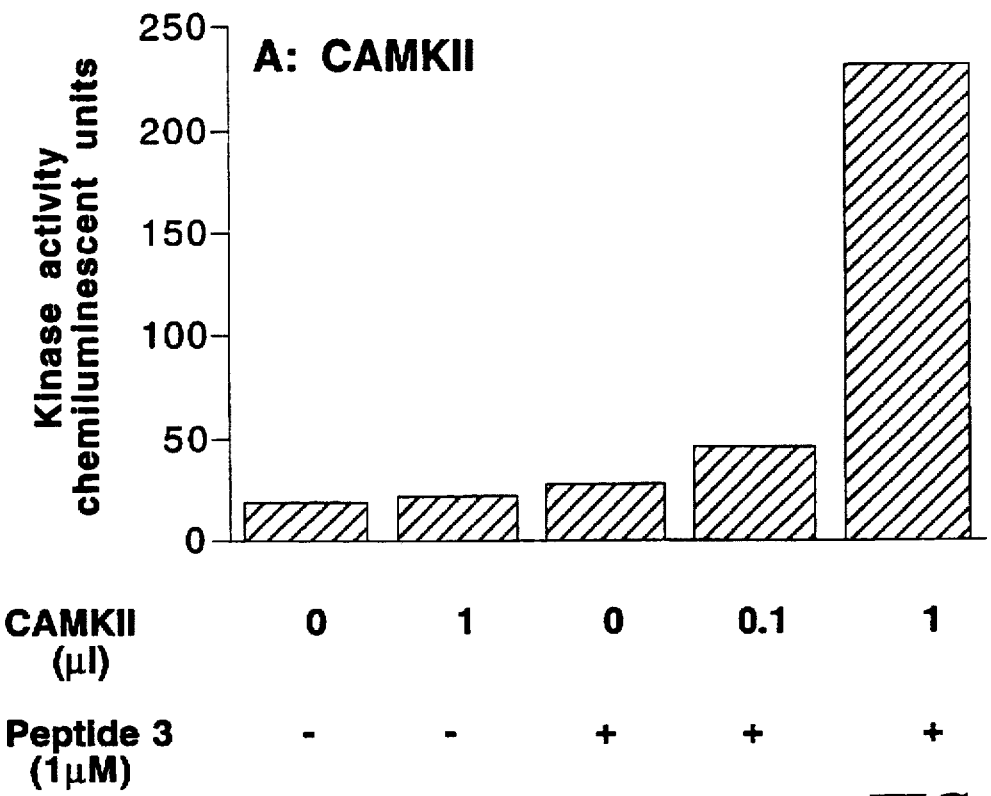
FIGS. 6A and 6B. Use of MPM-2 and 4G10 antibodies to detect activities of serine/threonine and tyrosine protein kinases.

Next we assessed the generality of the chemiluminescent detection method in the context of kinases with very different substrate specificity. MPM-2, a monoclonal antibody generated against mitotic proteins, and later shown to recognize a phosphorylated epitope has been used in numerous, mostly cell cycle related studies (22–24). Although it's exact epitope is not known, we tested whether this antibody could also function in the detection of substrate peptide phosphorylation. As FIG. 6A demonstrates, MPM-2 can detect activity of CAMK II (and presumably other kinases) when used with peptide 4 as kinase substrate.

Figure 6B:
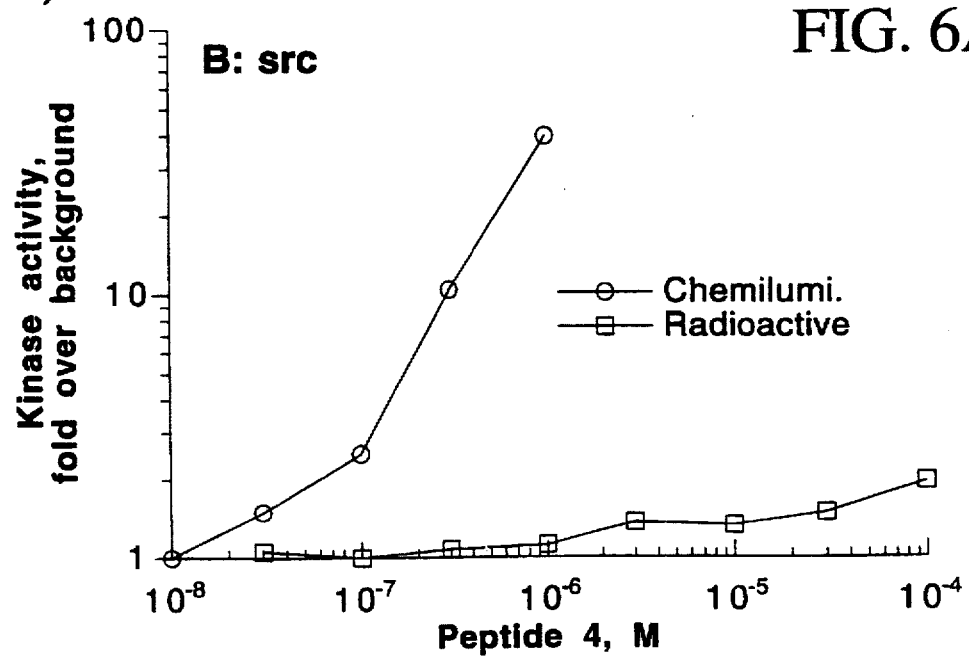

We tested whether chemiluminescent detection can provide a sensitive alternative method also for tyrosine kinases. Sensitive detection of tyrosine kinase activity by using peptide substrates is especially problematic because the $K_m$ of these peptides is frequently in the high micromolar range (2). Activity of these kinases has already been detected by colorimetric methods using anti-phosphotyrosine antibodies (14–18). To assess the usefulness of chemiluminescence for the detection of tyrosine kinase activity we used src and a biotinylated peptide [peptide 3, derived from the protein kinase RIP (21)] which we found to be the best substrate for this enzyme after screening several tyrosine containing peptides. This peptide still proved to have kinetically unfavorable properties when tested in a radioactive assay (FIG. 6B), similar to published data on other tyrosine kinase substrate peptides (2). In contrast, using the anti-phosphotyrosine antibody 4G10 and chemiluminescence for detection provided much higher assay sensitivity at a much lower peptide concentration (FIG. 6B).

Example 10: Discussion

The disclosed assay has many obvious advantages over the traditional radioactive protein kinase assay. All components of this assay can be stored for long periods of time with no loss in activity, and no radioactive waste is generated. The assay is also very fast and simple, the whole experiment can be easily accomplished in 2-3 hours. Since all steps are performed in one microtiter plate, automation is easier than with the radioactive assay requiring filtration and the use of corrosive materials. The chemiluminescent method also provided higher sensitivity than what was achievable by colorimetric detection, in accordance with results obtained by others comparing chemiluminescence and colorimetry (25-27). The robustness of the signal and the high sensitivity makes chemiluminescent detection a very good option for drug discovery efforts, such as high throughput screening.

The limitations of the radioactive kinase assay such as requirement for non-physiologically low ATP and high substrate concentrations, resulted in the discovery of many kinase inhibitors competing with ATP, but very few inhibitors with other characteristics. Most of these inhibitors appear very potent under such artificial assay conditions, but prove to be rather weak and quite toxic in a cellular environment. Furthermore, since they all target the well conserved ATP binding site of protein kinases, their selectivity is also generally poor. In contrast to the radioactive method, the chemiluminescent assay is much more robust at close to physiological ATP concentrations, providing much more realistic testing conditions.

Another drawback of the radioactive method is that its sensitivity strongly depends on a peptide substrate with low $K_m$. Efforts to identify such a peptide substrate for a novel kinase are time and energy consuming, and do not always result in success. It is especially true for tyrosine kinases, where the $K_m$ of peptide substrates is generally high (2). In contrast, the chemiluminescent assay provided a robust response even with substrates having high $K_m$ values, indicating that in case of a novel kinase efforts to identify a substrate with kinetically favorable properties may not be immediately required. Rather, the effort should be spent on identifying in vivo substrates. At present chemiluminescent assay conditions have been established for 8 kinases in our laboratory, and a highly sensitive high throughput drug screening operation is in progress for some of them.

Chemiluminescent detection resulted in a strong signal at $10^{-7}$M peptide concentrations, far below the $K_m$ of even the best peptide substrates. This, together with a requirement for low enzyme concentration, and also the robust response observed at high ATP concentration, indicate that among all presently available protein kinase assay methods chemiluminescent detection coupled with ELISA provides the highest sensitivity and best conditions to mimic the intracellular environment. Because of these favorable properties, application of this approach to drug discovery may result in the identification of novel classes of inhibitors not just for otherwise well characterized protein kinases, but also for recently discovered ones.

The described method has two limitations, but none of them are inherent. 1/ An antibody is required, distinguishing between the phosphorylated and non-phosphorylated peptide substrate. This is not a problem for tyrosine kinases, and recently more and more phosphoserine and phosphothreonine specific monoclonal and polyclonal antibodies have become commercially available. We also found that the YC10 and MPM-2 antibodies, used in this study, can detect the activity of kinases other than PKA, PKC, and CAMK II, using substrates with little similarity to peptides 2 and 4, respectively. Detailed characterization of the epitopes of these antibodies is in progress. Generation of additional antibodies recognizing phosphoserine or phosphothreonine in a well-defined, context dependent manner, is under way in our laboratory. Such antibodies could also be useful in determining the activity of a given protein kinase from complex samples (10). 2/ The streptavidin coated microtiter plate has limited peptide binding capacity. While a higher concentration of the substrate peptide is not required for the purpose of sensitivity, it would be required for determining the kinetic properties of the peptide, and also during the characterization of a test compound. This limitation can be overcome by using streptavidin coated beads with much higher biotin binding capacity.

Example 11: Parenthetical Numerically Cited References

1/ Casnellie, J. E. (1991) in Protein Phosphorylation. Part A. Methods in Enzymology vol. 200 (Hunter, T., Sefton, B. M., eds) pp. 115-120, Academic Press, San Diego 2/ Kemp, B. E., and Pearson, R. B. (1991) in Protein Phosphorylation, Part A. Methods in Enzymology vol. 200 (Hunter, T., Sefton, B. M., eds) pp. 121-134, Academic Press, San Diego 3/ Isbell, J. C., Christian, S. T., Mashburn, N. A., and Bell, P. D. (1995) *Life Sci* 57, 1701-1707

4/ Erdbrugger, W., Strohm, P., and Michel, M. C. (1995) *Cell Signal* 7, 635-642

5/ Lutz, M. P., Pinon, D. I., and Miller, L. J. (1994) *Anal. Biochem.* 220, 268-274

6/ McIlroy, B. K., Walters, J. D., and Johnson, J. D. (1991) *Anal. Biochem.* 195, 148-152

7/ Wang, Z. X., Cheng, Q., and Kililea, S. D. (1995) *Anal. Biochem.* 230, 55-61

8/ Zhao, Z. H., et al. (1991) *Biochem. Biophys. Res. Comm.* 176, 1454-1461

9/ Toomik, R., et al. (1993) *Anal. Biochem.* 209, 348-353

10/ Goueli, B. S., Hsiao, K., Tereba, A., Goueli, S. A. (1995) *Anal. Biochem.* 225, 10-17

11/ Boge, A., and Roth, R. A. (1995) *Anal. Biochem.* 231, 323-332

12/ King, I. C., Feng, M., and Catino, J. J. (1993) *Life Sci.* 53, 1465-1472

13/ Sista, P., et al. (1994) *Mol. Cell. Biochem.* 141, 129-134

14/ Schraag, B., et al. (1993) *Anal. Biochem.* 211, 233-239

15/ Farley, K., et al. (1992) *Anal. Biochem.* 203, 151-157

16/ Babcook, J., Watts, J., Aebersold, R., and Ziltener, H. J. (1991) *Anal. Biochem.* 196, 245-251

17/ Lazaro, I., et al. (1991) *Anal. Biochem.* 192, 257-261

18/ Angeles, T. S., et al. (1996) *Anal. Biochem.* 236, 49-55

19/ Geiser, T. H., Bergot, J. B., and Otteson, K. M. (1988) in Macromolecular Sequencing and Synthesis, Selected Methods and Applications (ed. Liss, A. R.) p. 199

20/ Fields, G. B. and Noble, R. L. (1990) *Int. J. Peptide Protein Research* 35, 161-214

21/ Hsu, H., et al. (1996) *Immunity* 4, 387-396

22/ Davis, F. M., et al. (1983) *Proc. Natl. Acad. Sci. U.S.A.* 80, 2926-2930

23/ Kuang, J., et al. (1994) *Mol. Biol. Cell* 5, 135–145

24/ Taagepera, S., et al. (1994) *Mol. Biol. Cell* 5, 1243–1251

25/ Van Poucke, S. O., and Nelis, H. J. (1995) *Appl. Environ. Microbiol.* 61, 4505–4509

26/ Gravel, P., et al. (1994) *Anal. Biochem.* 221, 66–71

27/ During, K. (1993) *J. Chromatogr.* 618, 105–131

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for detecting kinase activity in solution and without the use of radioactivity, said method comprising steps:

a) incubating a solution comprising a kinase, a first receptor, a nucleoside triphosphate and a substrate of said kinase wherein said substrate comprises a phosphorylation-independent first tag, under conditions whereby said kinase transfers a phosphate group from said nucleoside triphosphate to said substrate in solution to form a product comprising said first tag and a phosphorylation-dependent second tag;

b) further incubating said solution under conditions whereby said first receptor immobilizes said product on a solid substrate by specifically binding one of said first and said second tag to form a first immobilized conjugate comprising said first receptor and said product;

c) washing said solid substrate;

d) contacting said first immobilized conjugate with a second receptor under conditions whereby said second receptor specifically binds the other one of said first and said second tag to form a second immobilized conjugate comprising said first receptor, said product and said second receptor;

e) washing said solid substrate;

f) detecting said second receptor;

wherein the presence of said second receptor indicates the presence of said product and the presence of said product indicates the presence of said kinase activity.

2. A method according to claim 1, wherein all said steps are performed in a single tube.

3. A method according to claim 1, wherein said kinase is a protein kinase and said substrate comprises a peptide or polypeptide.

4. A method according to claim 1, wherein one of said first and second receptors is an antibody which specifically binds said product at said second tag.

5. A method according to claim 1, wherein said first tag is biotin and one of said first and second receptors is streptavidin.

6. A method according to claim 1, wherein said first tag is biotin, said first receptor is streptavidin and second receptor is an antibody which specifically binds said product at said second tag.

7. A method according to claim 1, wherein said second receptor comprises a label.

8. A method according to claim 1, wherein said second receptor comprises a label, said label comprises an enzyme, said enzyme catalyzes a chromogenic or chemiluminogenic reaction and said detecting step comprises detecting a color or luminescent change resulting from said reaction.

9. A method according to claim 1, wherein said detecting step comprises:

contacting said second immobilized conjugate with a third receptor under conditions whereby said third receptor specifically binds said second receptor to form a third immobilized conjugate comprising said first receptor, said product, said second receptor and said third receptor, and detecting said third receptor, wherein the presence of said third receptor indicates the presence of said second receptor.

10. A method according to claim 9, wherein said third receptor comprises a label.

11. A method according to claim 9, wherein said third receptor comprises a label, said label comprises an enzyme, said enzyme catalyzes a chromogenic or chemiluminogenic reaction and said detecting step comprises detecting a color or luminescent change resulting from said reaction.

\* \* \* \* \*